(12) United States Patent
Suzuki

(10) Patent No.: US 7,748,327 B2
(45) Date of Patent: Jul. 6, 2010

(54) MOVING DEVICE IN A PIPE LINE

(75) Inventor: Kazuhiro Suzuki, Takarazuka (JP)

(73) Assignee: Hi-Lex Corporation, Hyogo (JP)

( * ) Notice: Subject to any disclaimer, the term of this patent is extended or adjusted under 35 U.S.C. 154(b) by 374 days.

(21) Appl. No.: 11/780,354

(22) Filed: Jul. 19, 2007

(65) Prior Publication Data
US 2008/0115606 A1 May 22, 2008

(30) Foreign Application Priority Data
Jul. 19, 2006 (JP) .................. 2006-196616

(51) Int. Cl.
*B61B 13/10* (2006.01)
(52) U.S. Cl. .................... 104/138.2; 74/111
(58) Field of Classification Search .............. 104/138.2; 74/111
See application file for complete search history.

(56) References Cited

U.S. PATENT DOCUMENTS

| | | | | |
|---|---|---|---|---|
| 2,742,259 A * | 4/1956 | Boucher | ................. | 254/134.5 |
| 5,220,869 A * | 6/1993 | Pelrine et al. | ................. | 105/78 |
| 5,284,096 A * | 2/1994 | Pelrine et al. | ............ | 104/138.2 |
| 5,355,807 A * | 10/1994 | Pelrine et al. | ................. | 105/78 |
| 5,371,363 A * | 12/1994 | Lilimpakis | .................. | 250/253 |
| 5,388,528 A * | 2/1995 | Pelrine et al. | ................. | 105/78 |
| 5,601,025 A * | 2/1997 | Box | ........................ | 104/138.2 |
| 5,776,080 A * | 7/1998 | Thome et al. | ............... | 600/585 |
| 5,791,255 A * | 8/1998 | Box | ........................ | 104/138.2 |
| 6,667,677 B2 * | 12/2003 | Yajima et al. | ............... | 335/220 |
| 6,689,119 B1 * | 2/2004 | Di Caprio et al. | ........... | 604/523 |
| 7,441,507 B2 * | 10/2008 | Teraura et al. | ........... | 104/138.2 |
| 2003/0214580 A1* | 11/2003 | Iddan | .......................... | 348/81 |
| 2005/0284233 A1* | 12/2005 | Teraura et al. | ................ | 73/779 |
| 2008/0115606 A1* | 5/2008 | Suzuki | ........................ | 74/111 |

* cited by examiner

*Primary Examiner*—S. Joseph Morano
*Assistant Examiner*—Jason C Smith
(74) *Attorney, Agent, or Firm*—Browdy and Neimark, PLLC

(57) ABSTRACT

A moving device in a pipeline, including: more than three segments, including a front segment, arranged in series; an extendable interconnecting element to connect adjacent segments; and an engaging force changing component to change engaging force of a segment that is to be moved with the inside of the pipeline to a smaller force, smaller than the engaging force of a remaining segment with the inside of the pipeline. The front segment has a head part, a body part, a joint part to turn the head part centering around the body part, and a drive unit to move the head part around the body part. The drive unit have a magnet provided in the head part and an electromagnet provided in the body part.

11 Claims, 17 Drawing Sheets

Fig.1
(a)
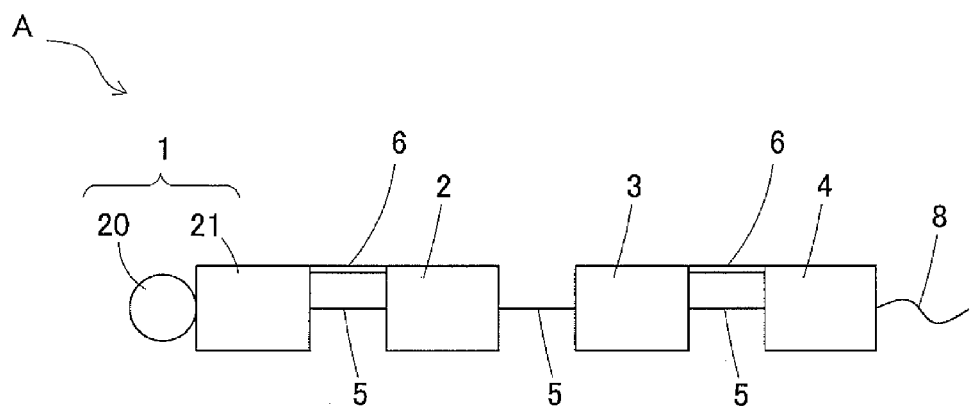
(b)
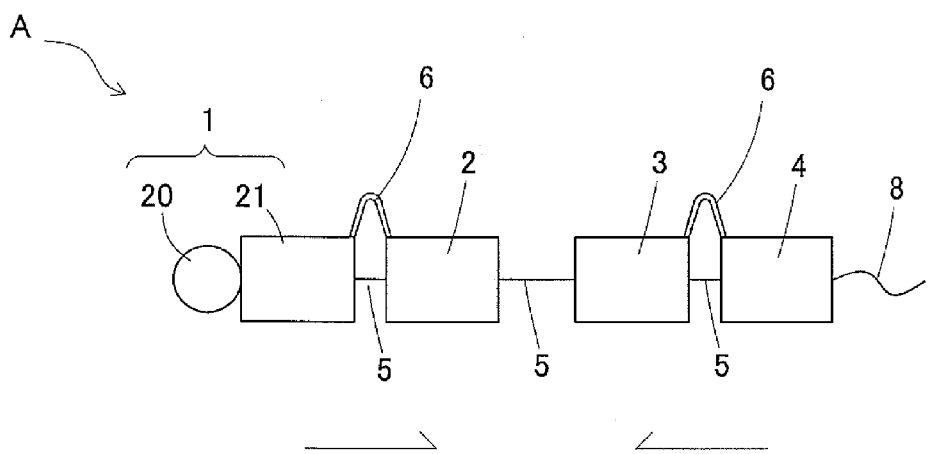

Fig.2
(a)
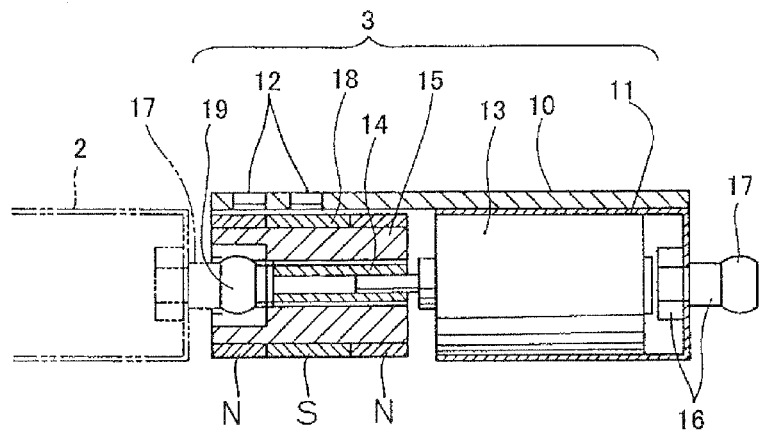
(b)
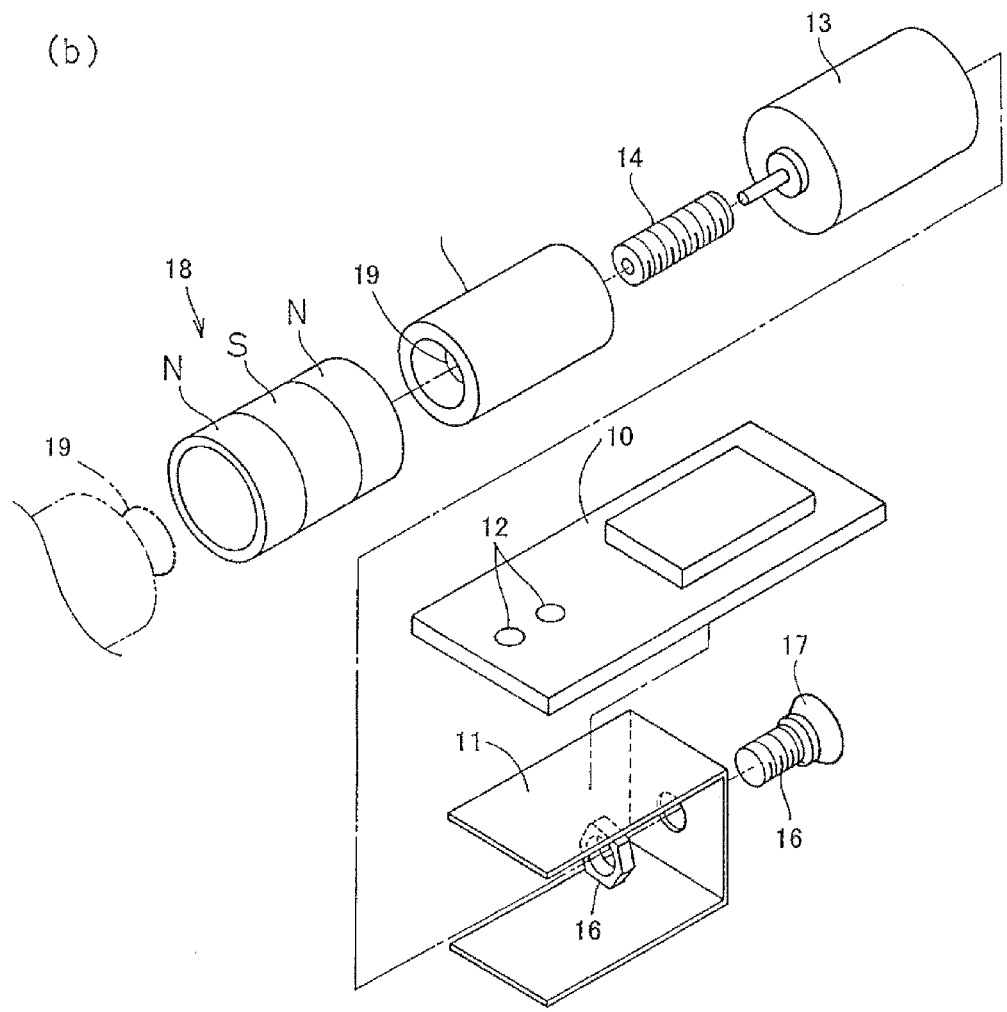

Fig.4
(a)
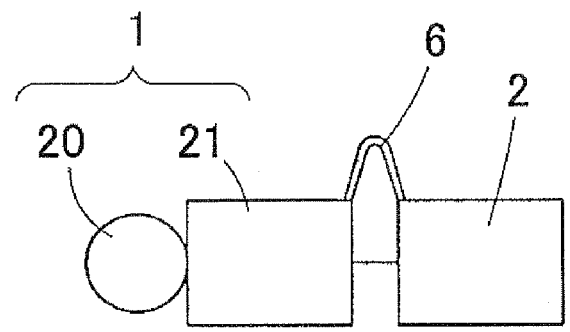
(b)
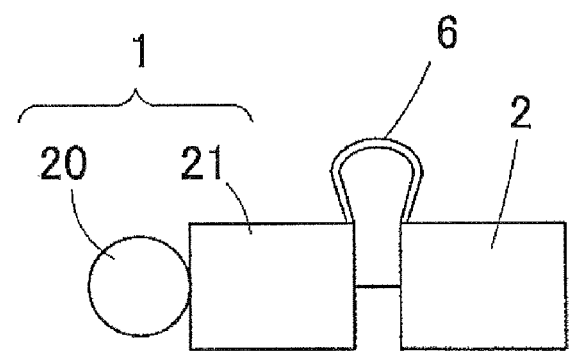

Fig.10
(a)
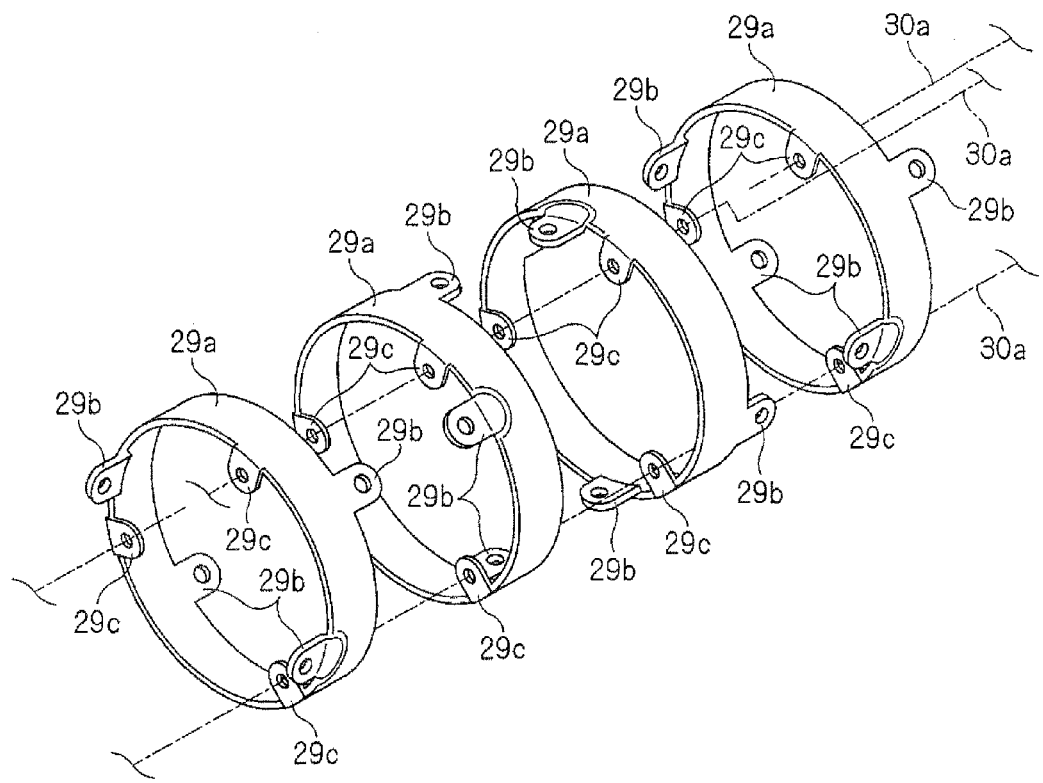
(b)
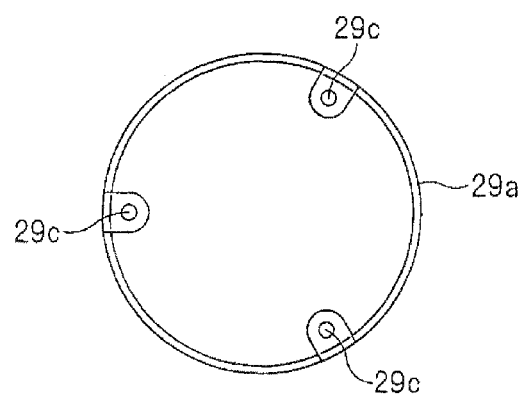

Fig.14
(a)
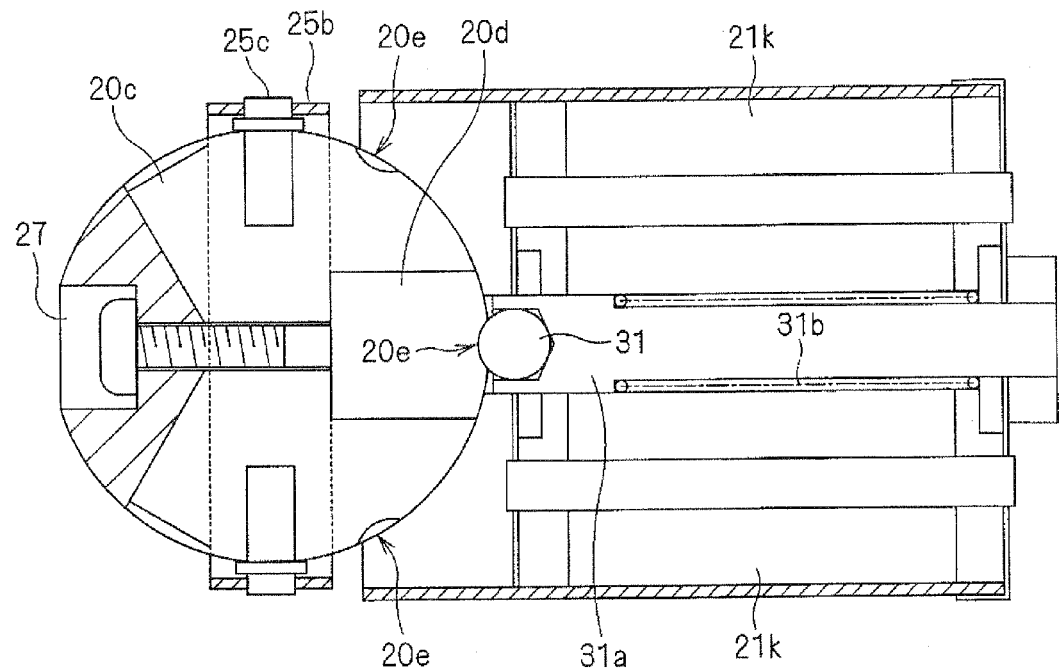
(b)
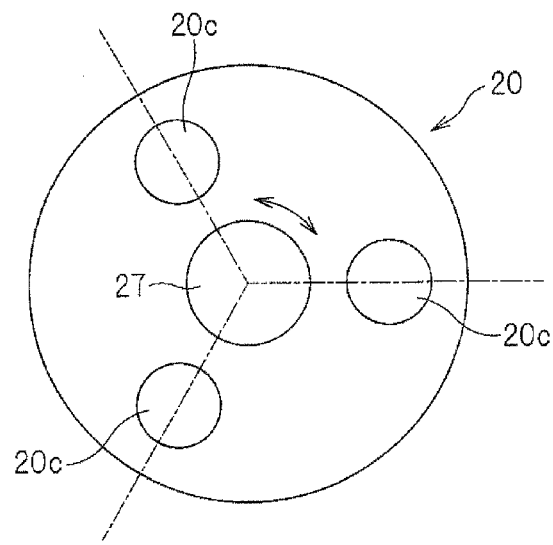

Fig.15
(a)
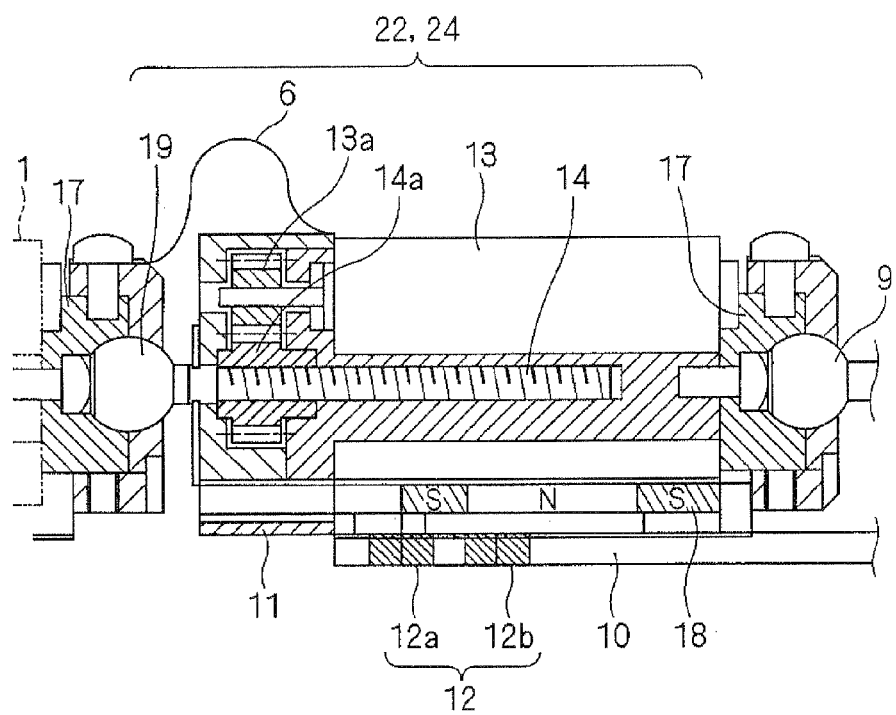
(b)
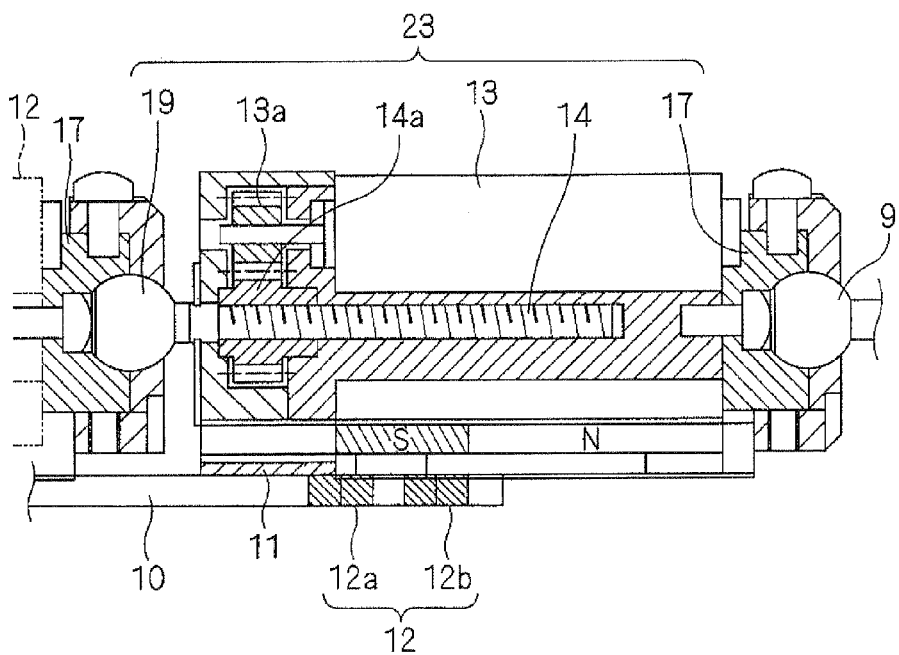

Fig.16
(a)
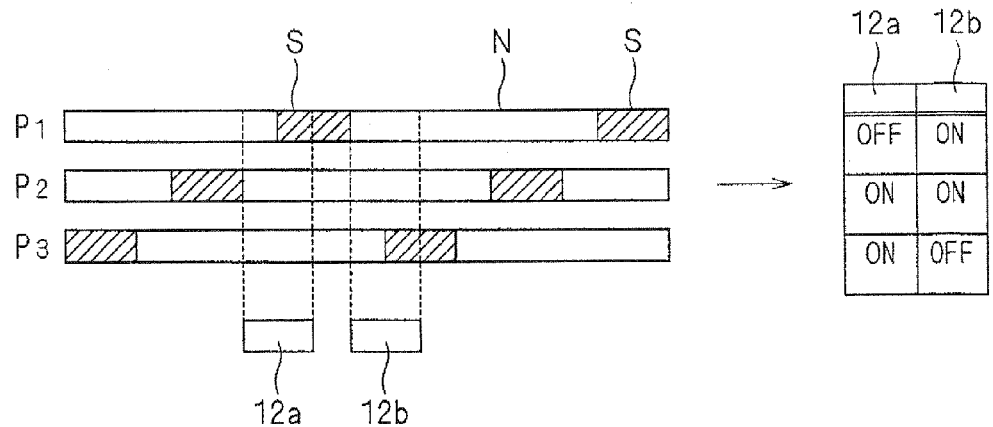
(b)
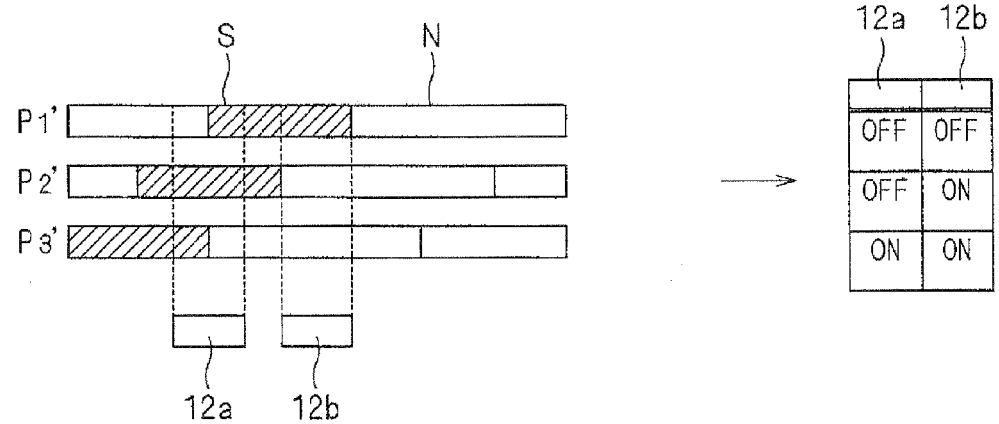

Fig.17
(a)
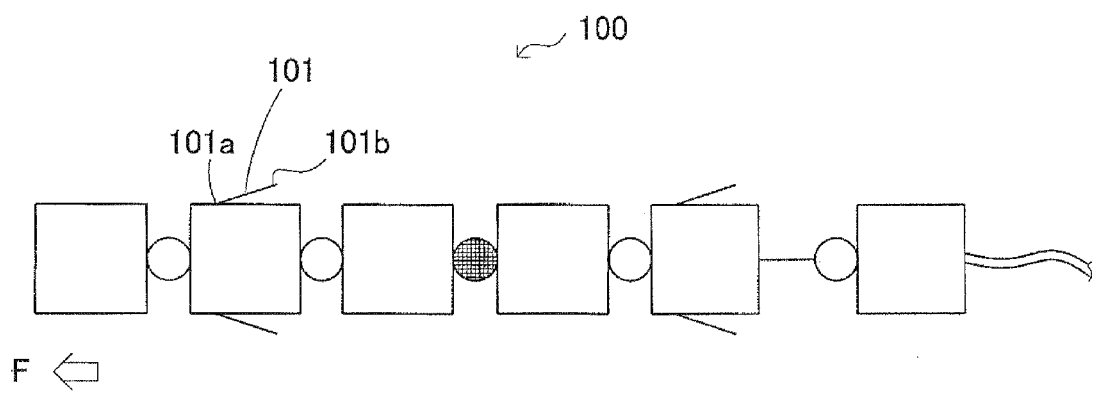
(b)
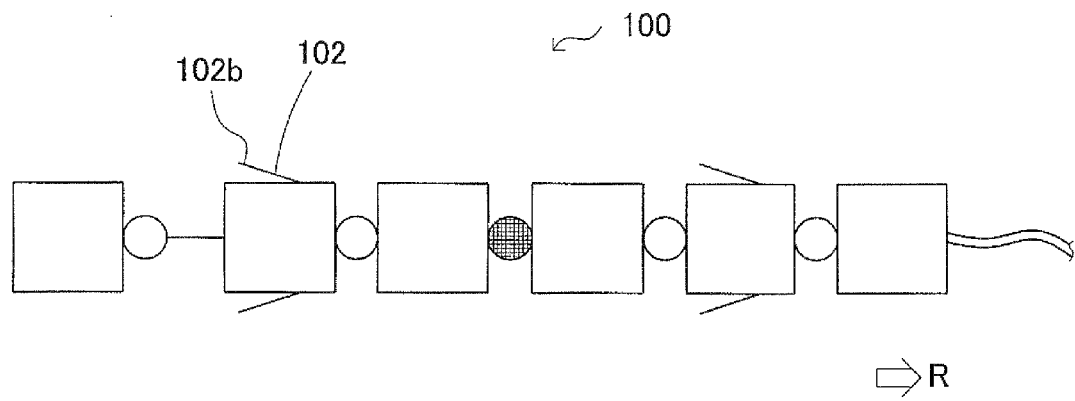

MOVING DEVICE IN A PIPE LINE

FIELD OF THE INVENTION

This invention relates to a moving device in a pipe line, for details, to a moving device to carry out move/halt by remote control or autonomously in body cavities or in pipe lines used for conveying various sensors to affected areas or repair portions, and for conveying and discharging medical agents such as curative medicines etc. and repairing agents etc. to repair the repair portions.

BACKGROUND ARTS

Patent Document 1: Japanese Published Patent Application No. 2000-219134
Patent Document 2: Japanese Published Patent Application No. 2004-359061
Patent Document 3: Japanese Published Patent Application No. H7-289504
Patent Document 4: Japanese Published Patent Application No. H5-344951
Patent Document 5: Japanese Published Patent Application No. 2002-153419

Since a moving device in pipe lines moves in the places where human's hand cannot reach, it must move smoothly in narrow pipe lines to reach a target position and must carry out an expected work or job at the target position.

Concerning how to move the moving device, there are some conventional technologies. The conventional moving device is characterized by how to obtain an engaging force with the inside of a pipe line. As the method of a conventional moving devices there is a method that a support section having partially a large engaging force with inside of a pipe line is fabricated in a moving device. And the support portion is made to be a scaffold, a free portion having small engaging force is moved against the support section.

The principle of the method is that the moving device is reciprocated in a pipe line, and the produced engaging force with the inside of the pipe line is adjusted so as to be larger in the forward direction than that in the backward direction by an anti-slip member. The adjustment of the engaging force makes the moving device become slippery in a desired direction. Such succession of the state of slipping in a slippery direction of the moving device appears as if moving in the pipe line. Two of such examples are cited bellow.

In Patent Document 1, a moving device in pipe lines using contraction/expansion of a bellows is described. At the front end and the rear end of the bellows, an anti-slip member presenting conical shape having its apex in the direction of forward movement is provided respectively. The anti-slip member has the engaging force with the inside of a pipe line to be lower in the forward direction and higher in the backward direction. When plus pressure/negative pressure is alternatively applied to the air or water inside of the bellows, the bellows contracts/expands. The difference of the engaging force in the forward movement and the backward movement of the anti-slip member by the contraction/expansion becomes a force to make the moving device move forward. And, when it is made to move backward, the direction of the anti-slip member of the conical shape is reversed so that its apex is aimed at the backward direction. When it is reversed, while the moving device is halted, the moving device is pulled by a tube for letting air in and out of the bellows to change the direction of the anti-slip member.

The moving device shown in Patent Document 2 performs a kind of reciprocating movement by broadening or narrowing sequentially the distance between a plurality of segments. In the side of the segments, two kinds of rod-like arm for forward movement and backward movement in parallel to the reciprocating movement are attached. The moving device shown in FIG. 17*a* is the outline drawing of an arrangement of the arm when moving forward (reference numeral F). The arm 101 for forward movement is locked so that the end portion of the forward movement side is made to be the base end 101*a* at the side of the segment, and the end portion of the opposite side is extended outward as a free end 101*b* when the moving device 100 moves forward. On the other hand, in FIG. 17*b*, the arrangement of the arm is shown when the moving device 100 is moving backward (reference numeral R). The arm 102 for backward movement is attached in the opposite direction to the arm for forward movement, and extends the free end 102*b* of the forward movement side when being in the backward movement. Thus, the arm is formed so that it is like a truncated chevron shape narrowed from outward to inward as it goes along the direction of movement. Hence, in the direction of movement, the engaging force with the inside of a pipe line is small, and in the opposite direction, the portion broaden as the truncated chevron shape becomes the engaging force with the inside of the pipe line.

In Patent Document 3, a capsule endoscope equipped with balloons in its front and rear and equipped with a self advancing portion interconnecting them by an extendable bellows is disclosed. In the self advancing portion, for example, by its front balloon being expanded and fixed to the inside wall of duodena and its rear side balloon being contracted to retract the bellows, the rear side bellows can be moved forward. Then, by its rear side balloon being expanded and fixed to the inside wall and its front side balloon being contracted to extend the bellows, the front side balloon can be moved forward. And repeating these series of the process sequentially, it can be moved forward intermittently. Moreover, performing these series of the process in the reverse sequence, the self advancing portion can be stepped back.

There is an equipment in Patent Document 4, in which, after the moving device reaches the target position, for example, photographing is carried out by turning a camera to the direction of arbitrary visual field. In the body of the equipment, a plurality of transducers which is vibrated by an ultrasonic motor is provided, and the camera is housed in a spherical body, and is turned by the vibration of the transducers.

In Patent Document 5, an endoscope is disclosed, in which a rotation body with an installed camera is rotated in a body cavity, and the condition of inside of the body cavity can be observed. The rotation body presents about egg shape and is housed in a capsule base body of cup shape. In the inside perimeter surface of the capsule base body, an electromagnetic coil is arranged. On the other hand, in the periphery of the rotation body, magnets are adhered so that the magnetic polarity is alternated to be as N-S-N-S••. Hence when the current of predetermined pulses is applied to the electromagnet of the capsule base body, the rotation body can be rotated against the capsule base body like a pulse motor.

DISCLOSURE OF INVENTION

In the moving device of Patent Document 1, when making the transition from the forward movement to the backward movement, it is necessary to pull the moving device itself by pulling the near side of the tube in order to reverse the conical shape anti-slip member. If it is in the environment that such work can be transferred directly to the moving device, there may be no problem. But when the path in pipe lines forms a weblike pattern, it is hard for the operating physical force from the near side to be transferred to the moving device.

The moving device of Patent Document 2 opens corresponding arms in response to the forward movement or the backward movement. Hence, number of parts increases and the structure becomes complicated. The self advancing portion of the capsule endoscope of Patent Document 3 can perform both the forward movement and the backward movement by the remote control of the balloon and the bellows. However, it takes long time for injection and exhaust of air or liquid to the balloon or the bellows.

The technology of Patent Document 1, 2 makes the shape of the anti-slip member be a stream line taken along the direction of movement. By making it be such a stream line, the engaging force in the direction of forward movement is decreased, and the difference of the engaging force between the forward movement and the backward movement is taken out as a force for the forward movement. The engaging force generated between the moving device and the surface of the inside of a pipe line is considered to be depending on "friction" between the moving device and the surface of the inside of a pipe line or "scratch" by the shape between the moving device and the surface of the inside of a pipe line. To increase the "friction", it is preferable for the moving device to push the inside of a pipe line with a large force. To enhance the "scratch", it is preferable for the moving device to protrude its engaging portion with the inside of a pipe line largely. By satisfying these, the engaging force can be increased to enlarge the difference of the engaging force in the forward movement and the backward movement.

However, under such circumstance as Patent Document 3, it takes a lot of trouble so far forth as to try for the "friction" and the "scratch" securely. And, such one cycle as "performing friction and scratch, and then extension and retraction" is prolonged. As described above, to carry out the "friction" and the "scratch" and the performance of movement is in a relation opposite to each other.

In Patent Document 4, a vibrator is used for turning the camera, but the structure is complicated. In Patent Document 5, electromagnets are used in the periphery of the rotation body causing the whole body to become large. Further, this is not possible to be moved forward or pulled back in pipe lines.

Consequently, the moving device of this invention is directed to provide a moving device which can obtain securely an engaging force with the inside of a pipe line using a simple mechanism and can perform smoothly the forward movement and the backward movement, and at the same time, to provide a moving device which can change the direction of the head in a pipe line with a simple mechanism.

The first embodiment of the moving device in pipe lines of this invention (claim 1) comprises more than three segments including a front segment arranged in serial; an extendable interconnecting means to connect adjacent segments; and an engaging force changing means to change an amount of an engaging force of the segment which is to be moved with an inside of the pipe line to smaller amount, smaller amount than the engaging force of the remaining segment with the inside of the pipe. It further recites that the front segment have a head portion, a body portion, a joint part to turn the head part centering around the body part, and a drive unit to move the head part around the body part, and the drive unit have a magnet provided in the head part and an electromagnet provided in the body part.

In such moving device, it is preferable that plural of the magnet is provided around an axis of a moving direction of the head part at equal intervals, and plural of the electromagnet is provided around an axis of a moving direction of the body part at equal intervals, wherein numbers of the magnet and the electromagnet are same (claim 2).

Further, it is preferable that more than four segments are arranged serially, and an engagement member bridging adjacent segments is provided between at least more than two adjacent segments, and when the extendable interconnecting means interconnecting the adjacent segments bridged by the engagement member retracts, the engagement member bends and a bended part of the engagement member protrude outwardly engaging with the inside of the pipe line (claim 3).

Moreover, it is further preferable that the front segment, a second segment, a third segment, and a forth segment are arranged in serial, and the engagement member bridging the adjacent segments is provided between the front segment and the second segment, and the third segment and the forth segment (claim 4).

A moving device where the head part of the front segment presents a rough spherical shape, and is mounted with a camera, a cleaning nozzle, or a touch switch, and the joint part is an universal joint is also preferable (claim 5).

The second embodiment of the moving device of this invention (claim 6) comprises more than three segments including a front segment arranged in serial; an extendable interconnecting means to connect adjacent segments; and an engaging force changing means to change an amount of an engaging force of the segment which is to be moved with an inside of the pipe line to smaller amount, smaller amount than the engaging force of the remaining segment with the inside of the pipe. This moving device also recites that the front segment have a head portion, a body portion, a joint part to turn the head part centering around the body part, and a drive unit to move the head part around the body part, and the drive unit have an inner cable interconnecting the head part and the body part, an inner cable rocking portion provided in the head part, a motor portion provided in the body portion, and the head part is turned around the body part by pulling in or sending out the inner cable by the motor portion.

In such moving device, it is preferable that the inner cable, the inner cable locking portion of the head part, and the motor portion of the body part as a set are arranged respectively around an axis of a moving direction and more than three sets are arranged respectively at equal intervals in the axis of the moving direction (claim 7). Moreover, it is further preferable that more than four segments are arranged serially, and an engagement member bridging adjacent segments is provided between at least more than two adjacent segments, and when the extendable interconnecting means interconnecting the adjacent segments bridged by the engagement member retracts, the engagement member bends and a bended part of the engagement member protrude outwardly engaging with the inside of the pipe line (claim 8). Further, the moving device may be composed of the front segment, a second segment a third segment, and a forth segment arranged in serial, and the engagement member bridging the adjacent segments may be provided between the front segment and the second segment, and the third segment and the forth segment (claim 9). And moreover, the head part of the front segment may present a rough spherical shape, and may be mounted with a camera, a cleaning nozzle, or a touch switch, and the joint part may be an universal joint (claim 10).

In the moving device in pipe line of this invention, in which the moving device comprises more than three segments including a front segment arranged in serial, an extendable interconnecting means to connect adjacent segments, and an engaging force changing means to change an engaging force of the segment which is to be moved with an inside of the pipe line to a smaller force, smaller than the engaging force of the remaining segment with the inside of the pipe line, wherein the front segment have a head part, a body part, a joint part to turn the head part centering around the body part, and a drive unit to move the head part around the body part, wherein the drive unit have a magnet provided in the head part and an electromagnet provided in the body part, the interval of the mutual segments extends and retracts by the extendable interconnecting means. In this occasion, the engaging force adjusting means changes the engaging force of the segment with the inside of the pipeline to smaller force, smaller than the engaging force of the remaining segment with the inside of the pipe line, therefore, the segments in which the engaging force had been changed, can move to the direction of the movement in the pipe line against the remaining segments. And, when it arrives at a target position, the head part of the front segment can be turned around the body by turning on the electricity of the electromagnet of the body. Hence, the head can be led to the detailed position of the target position, an exact treatment can be dispensed at the target position.

In such moving device having plural of magnets provided around an axis of the moving direction of the head part, and plural of the electromagnet provided around the axis of the moving direction of the body part at an equal intervals, and the numbers of the magnet and the electromagnet are same, the turning motion of the head part is secure.

In the case where more than four segments are arranged in serial, and an engagement member bridging adjacent segments is provided between at least more than two adjacent segments, where the extendable interconnecting means interconnecting the adjacent segments bridged by the engagement member retracts, the engagement member bends and a bended part of the engagement member protrude outwardly engaging with the inside of the pipe line, the engagement member extends outwardly when the space between the segments in which the engaging member are interconnected is retracted by the extendable interconnecting means. The extended portion of the engaging member presses the inside of the pipe line and generates the engaging. The engaging force is the "friction" obtained by pressurizing the inside of the pipe line with the engaging member and the "scratch" by extending in the inside of the pipe line. If at least one engaging member is pressed to the inside of the pipe line, segments which is not being held by the engaging force can move against the segments being held by extending or retracting the extendable interconnecting means provided between the segments. After that, when the engaging with the inside of the pipe line is turned over to the other engaging member, the segment interconnected with the previously engaged engaging member can move against the segment interconnected with the other engaging member which is now being held by extending the extendable interconnecting means between the segment interconnected with the previously engaged engaging member which was held in retracting condition until now. Repeating such motions, the moving device can move forward or backward. And, the engaging member can be made to be plural according to the engaging force with the inside of the pipe line.

In the case where the front segment, a second segment a third segment, and a forth segment are arranged in serial, and the engagement member bridging the adjacent segments is provided between the front segment and the second segment, and the third segment and the forth segment, very compact moving device having a minimum configuration having four segments and the two engaging members can be obtained.

In the case where the head part of the front segment presents a rough spherical shape, and is mounted with a camera, a cleaning nozzle, or a touch switch, and the joint part is an universal joint, the inside of a pipe line can be checked in every corner and treatments can be dispensed, because the head can be turned to any direction.

The second embodiment of this invention, in which the moving device comprises more than three segments including a front segment arranged in serial, an extendable interconnecting means to connect adjacent segments, and an engaging force changing means to change an engaging force of the segment which is to be moved with an inside of the pipe line to smaller force, smaller than the engaging force of the remaining segment with the inside of the pipe line, wherein the front segment have a head part, a body part, a joint part to turn the head part centering around the body part, and a drive unit to move the head part around the body part, wherein the drive unit have an inner cable interconnecting the head part and the body part, an inner cable locking portion provided in the head part, a motor portion provided in the body part, and wherein the head part is turned around the body part by pulling in or sending out the inner cable by the motor portion, has the same effect as the first embodiment regarding the moving method of the moving device, and since the head part can be turned around the body part by using the inner cable, the structure is simple. Moreover, the use of the inner cable enables to turn the head even when the head and the body are at distant.

In such moving device, where the inner cable, the inner cable locking portion of the head part, and the motor portion of the body part as a set are arranged respectively around an axis of a moving direction and more than three sets are arranged respectively at equal intervals in the axis of the moving direction, the turning motion of the head part is secured.

When the head part of the front segment presents a rough spherical shape, and is mounted with a camera, a cleaning nozzle, or a touch switch, and the joint part is an universal joint, the inside of a pipe line can be checked in every corner and treatments can be dispensed, since the head can be directed to any direction.

BEST MODE FOR CARRYING OUT THE INVENTION

Next, referencing the drawings, the embodiments of the moving device in pipe lines of this invention are described.

FIGS. 1a, 1b are pattern diagrams showing the outline of the moving device of this invention.

FIG. 2a is a side cross sectional view showing an embodiment of extendable interconnecting means, FIG. 2b is an exploded perspective view of FIG. 2a.

FIG. 4a and FIG. 4b are rough drawings showing the aspect of the engaging member being bent.

FIG. 10a is a partial perspective view showing the flexible joint of FIG. 9, FIG. 10b is A arrow view of FIG. 10a.

FIG. 14a is a partial cross sectional view of FIG. 13, FIG. 14b is a pattern diagram seeing the arrangement of the magnet from the direction of movement.

FIG. 15a is a partial cross sectional side view showing the connection of the first segment and the second segment, FIG. 15b is a partial cross sectional side view showing the connection of the second segment and the third segment.

FIG. 16a and FIG. 16b are pattern diagrams showing the position of the magnet and the detecting state of the position sensor based on the working state of the each extendable member of the second segment and the third segment.

FIG. 17a shows the arrangement of the arm when the moving device is moving forward.

FIG. 17b shows the arrangement of the arm when the moving device is moving backward.

Figure 3:
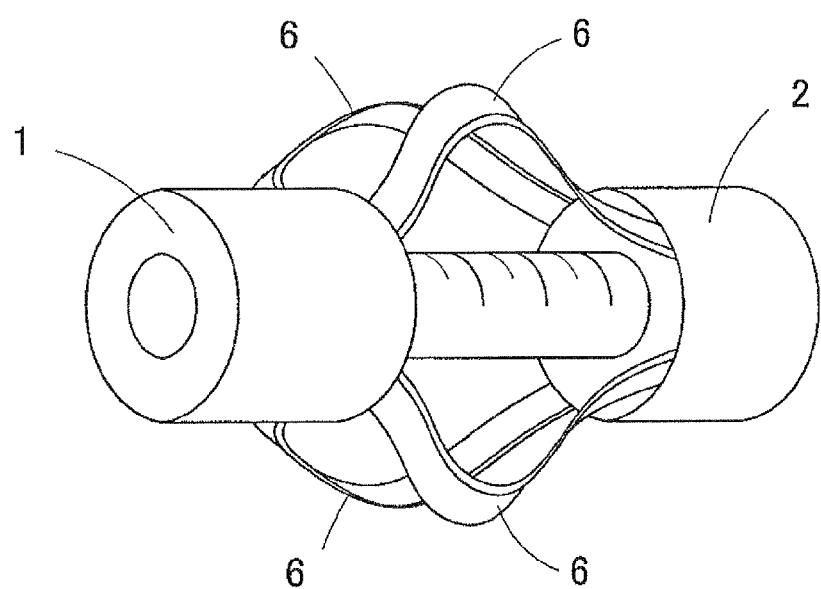
FIG. 3 is a rough perspective view of the engaging member.

First, the moving device A of FIG. 1a shows a fundamental embodiment of the moving device of this invention. The moving device A comprises four segments. Starting from the left, it is the first segment (front end segment) 1, the second segment (secondary) 2, the third segment (ternary) 3, and the forth segment (rear end) 4 respectively in sequence. These segments are interconnected in series by extendable members (extendable interconnecting means) 5, 5, 5 having retractility. And, between the first segment 1 and the second segment 2, and between the third segment 3 and the forth segment 4, engaging members 6, 6 are provided. Further, to the forth segment 4, an electric wire 8 is connected for electric power to extend or retract the extendable member 5 or for communication. The first segment 1 comprises a head part 20 equipped with later described camera etc. and a body part 21 having a drive portion for swinging the camera mounted on the head part. Magnets and inner cables may be used in the drive portion, which is described later.

The moving device shown in FIG. 1a is in the state that all extendable members 5, 5, 5 are extended. In this occasion, the engaging members 6, 6 are also in the state of being extended. When the extendable member 5 between the first segment 1 and the second segment 2, and the extendable means 5 between the third segment 3 and the forth segment 4 are retracted from this state as shown in FIG. 1b, both end segments 1, 4 can be pulled inside without being affected by the engaging force of the moving device with the inside of the pipe line. Additionally, an engaging force changing means is composed by the extendable member 5 and the engaging member 6.

The material of the segment 1, 2, 3, and 4 are selected corresponding to the inside of the pipe line being used. Particularly, when the pipe line is the interior of the body such as human and animal, it is preferable to be composed of materials having biocompatibility such as stainless, titanium, or ceramic, and particularly titanium is preferable to be used. Moreover, the segment may be coated with a biocompatible material. As the extendable means 5 to extend of to retract the intervals between each segment, motors can also be used, and it may be what brings about the similar effect such as a voice coil motor, water pressure or oil pressure cylinder.

In the first segment 1, a touch switch, a camera, a cleaning nozzle, or nozzle for blowing out air are provided in its front end portion. Inside of the first segment 1, medical agents such as curative medicines etc. and repairing agents etc. for repairing the repair portions are housed, and by the touch switch, those are discharged and the like. The touch switch has a controller and performs automatic halt etc. by detecting the dead end in the pipe line.

Next, using FIG. 2a and FIG. 2b, the embodiment of the segment 2, 3, 4 and the extendable member 5 are shown. In FIG. 2a and FIG. 2b, the second segment 2, the third segment 3, and the extendable member 5 interconnecting those segment mutually are shown. Since the each segment and the extendable member 5 are common in many portions, the third segment and the extendable member 5 provided there are described and other portions are omitted in the description. In the third segment 3, the extendable member 5 and a driver 10 to control the extendable member 5 are arranged. The extendable member 5 is arranged in a casing 11 which is a plate-like member folded into U shape, and on the upper surface of the casing 11, a substrate equipped with the driver 10 is mounted. In the one end of the driver 10, a position sensor 12 (magnetic sensor) is mounted, and the portion for detecting magnetic force is protruded form the periphery of the casing 11 crossing over the opening end.

The extendable member 5 comprises a motor 13, a male screw 14 to be attached to the axis of the motor 13, and a nut 15 which screws together with the male screw 14 and moves toward the direction of the axis (forward and backward direction) rotating on the male screw 14. The motor 13 is fixed to the bottom of the casing 11 at its rear portion using a cramping device 16 consisting of a bolt and nut. To the bolt of the cramping device 16, a socket 17 of ball joint is attached.

The nut 15 is covered by a cylindrical magnet 18 which can be fitted to its periphery. In the vicinity of the center of the cylindrical magnet 18 is magnetized to be belt-like S pole. The right and left of the belt-like S pole are magnetized to be belt-like N pole. In the front end portion of the nut 15, the socket 17 of the ball joint is provided, which houses therein a ball 19 attached to the vicinity of the bottom of the casing 11 of the front second segment 2 and interconnects the ball 19 rotatably. Between the ball 19 of ball joint and the socket 17, a friction resistance is applied so as to make the nut 15 not rotate when the male screw 14 rotates.

Next, the aspect of motion of the extendable member 5 is described. First, the motor 13 runs. Then the male screw 14 rotates and the nut 15 screwing together with the male screw 14 moves in the axial direction while rotating. Resultantly, the front second segment 2 is pushed by the ball 19. And, since the cylindrical magnet 18 moves in the axial direction on the male screw 14 together with the nut 15, a position sensor 12 catches the change of the magnet pole and detects the end of the motion of the extendable member 5.

Next, the engaging members 6, 6 are described. Since those engaging members 6, 6 are in common, the engaging members 6 between the segment 1, 2 is described, and the description about the engaging members 6 between the segments 3, 4 will be omitted. The engaging members 6 shown in FIG. 3 are tabular or sheet-like members. Four of those engaging members 6 are provided in the periphery of the segment at equal intervals between the first segment 1 and the second segment 2. The number of the engaging member is 2-8, and is preferable to be 4-6 in order to be capable of arranging equally in right and left, above and bellow. As the material for the engaging members 6, for example, stainless, preferably titanium or metal such as titanium alloy, synthetic resin such as polyethylene (PE), polypropylene, having flexibility and suitable rigidity having only a little effect on the human body may be used.

When the extendable member 5 between the first segment 1 and the second segment 2 retracts, the engaging member 6 shifts from the straight line state (see FIG. 1a) to the bent state (see FIG. 1b). The vicinity of the apex of the bent engaging member 6 presses or scratches the inside of the pipe line to generate the engaging force with the inside of the pipe line. Moreover, when convexoconcave shape is formed in the contacting portion of the engaging member 6 and the inside of the pipe line, the friction with the inside of the pipe line can be made large.

The bent state of the engaging member 6 can be changed by changing its material or elasticity. Such examples presenting the bent state are shown in FIG. 4a and FIG. 4b. The engaging member 6 shown in FIG. 4a bends in a sharp angle when bending. Hence, in the pipe line having soft inside, it protrudes outward largely and scratches the inside of the pipe line making it possible to obtain a large engaging force. And, the engaging member 6 of FIG. 4b bends in an obtuse angle when bending. Hence, it contacts by a large area with the inside of a pipe line, the friction force with the inside of the pipe line is increased making it possible to obtain a large engaging force. In addition, as the engaging member 6, a tabular member was used, but a rod-like member, a hinge or a mesh, or a chain can be also used.

The wire 8 is a power line to supply electric power to the motor 13 of the each segment or a communication line to interconnect the drivers 10 making them capable of communicating each other. A controller is connected to the end (not shown in the figure) of the wire 8, and the instruction of forward movement and backward movement can be executed. The driver 10 controls how to operate the own extendable member 5 based on the detected value sent from the position sensor 12 of other segments and the own segment.

Moreover, in the case that the driver 10 is equipped with a mechanism to change the amount of extension/retraction of the extendable member 5, the engaging force maybe enlarged by retracting the extendable member largely and let the extendable member protrude outward, when the engaging force is not enough. On the other hand, when the engaging force is secured enough, the amount of the extension may be decreased for the rapid motion.

Further, in the case that the driver 10 is equipped with a mechanism capable of detecting whether or not an amount of torque for the movement of the segment detected is smaller than a predetermined amount, it is possible to identify that the moving device is not moving while the pushing segment and the pushed segment are only sliding mutually in the opposite direction in the pipe line. In this case, the amount of extension may be increased by making the engaging member protrude largely to give a large engaging force to the moving device A.

Figure 5:
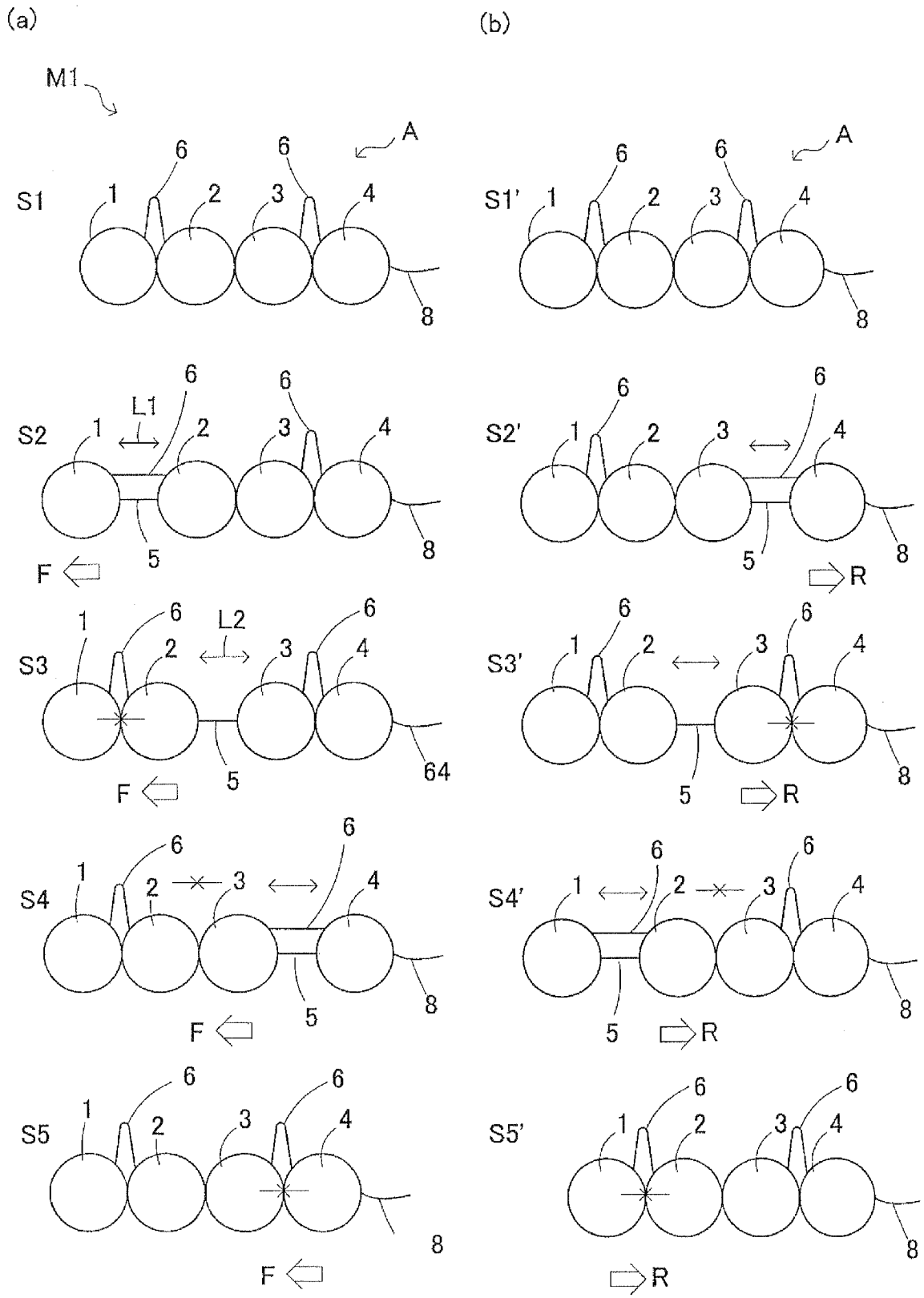
FIG. 5a and FIG. 5b are respectively pattern diagrams showing the aspect of the forward movement and the backward movement of the moving device.

The aspect of the movement of the moving device A composed as above is described using FIG. 5. In FIG. 5, the moving method M1 of the moving device A is shown. In the figure, the portion where the segments are contacted mutually shows the retracted state of the extendable member 5, and the extendable member 5 is shown in the figure only when it extends. First, all the extendable members 5 retracts and the engaging members 6, 6 bend to engage with the inside of a pipe line. This state is made to be a starting state (S1). From the starting state (S1), there is a process (S2) to broaden the interval between the segment 1, 2 by extending the extendable member 5 arranged between the first segment 1 and the second segment 2. In this occasion, the engaging member 6 between the segment 1, 2 becomes a straight line state, but since the engaging member 6 between the segment 3, 4 holds the engaging force with the inside of the pipe line at a sharp angle bent portion, the first segment 1 moves inside of the pipe line against the engaging member 6 toward the arrowhead F side (left side) of the figure. Additionally, it is made to be the start state (S1), but it may be started from the process S3 to begin the forward movement and the backward movement.

And then, there is a process (S3) to retract the extendable member 5 between the first segment 1 and the second segment 2, and to extend the extendable member 5 arranged between the second segment 2 and the third segment 3. In the process S3, the second segment 2 retracts the interval in between the first segment 1 and broadens the interval in between the third segment 3. Resultantly, by the engaging force of the engaging member 6 between the segment 3, 4 and the inside of the pipe line, the second segment 2 is pulled toward the first segment 1 side. In this occasion, the engaging member 6 between the segment 1, 2 becomes again the state of being bent generating the engaging force with the inside of the pipe line. Then, the extendable member 5 between the second segment 2 and the third segment 3 is retracted, and the extendable member 5 between the third segment 3 and the forth segment 4 is extended (S4). Last of all, the interval of the extendable member 5 arranged between the third segment 3 and the forth segment 4 is retracted to move the forth segment 4 toward the arrowhead F side and to pull it toward the third segment 3 side (S5). In this case, as a reaction of the engaging force of the engaging member 6 between the segment 1, 2, the third and the forth segment 3, 4 move. When this process is completed until S5, it returns to S1. Repeating such processes, the moving device moves in the pipe line toward the arrowhead F direction.

When this moving device A is made to move backward, as shown in FIG. 5b, from the forth segment 4 of the rear end to the first segment 1 in a sequential order, they are operated from S1' to S2', S3', S4', S5' in the reverse order of the prior sequence. And, after the motion of the S5 ends, by repeating the process such as to begin from the S1, the moving device A moves in the pipe line toward the arrowhead R side.

In the moving method M1 shown in FIG. 5, the interval of the extension/retraction of the mutual adjacent segments is constant. For example, the extension/retraction interval L1 (see S2 of FIG. 5a) of the first segment 1 and the second segment 2 and the extension/retraction interval L2 (see S3 of FIG. 5a) is much the same. More specifically, when the second segment 2 moves forward the first segment 1 as long as L1, the second segment 2 following the first segment 1 moves forward to the first segment 1, spacing the interval L2 ($\approx$L1). For the following third second segment and the forth segment, the condition is much the same. As the extension/retraction interval L1, an extension/retraction interval (stroke) so as to bend the engaging member 6 until to be capable of obtaining a predetermined engaging force with the inside of the pipe line is necessary.

The length of the engaging member 6 bridged in between the interval L1 is much the same with the interval L1 though there is a certain degree of expansion and contraction due to the elastic deformation of the material. Thus, when the moving device A is operated by the moving method M1, since the each segment or engaging member performs almost the same motion, common parts become many. Thereby, the repair and the replacement are easy. Further, since the motion of forward/backward movement is easy, the control is also easy.

Figure 6:
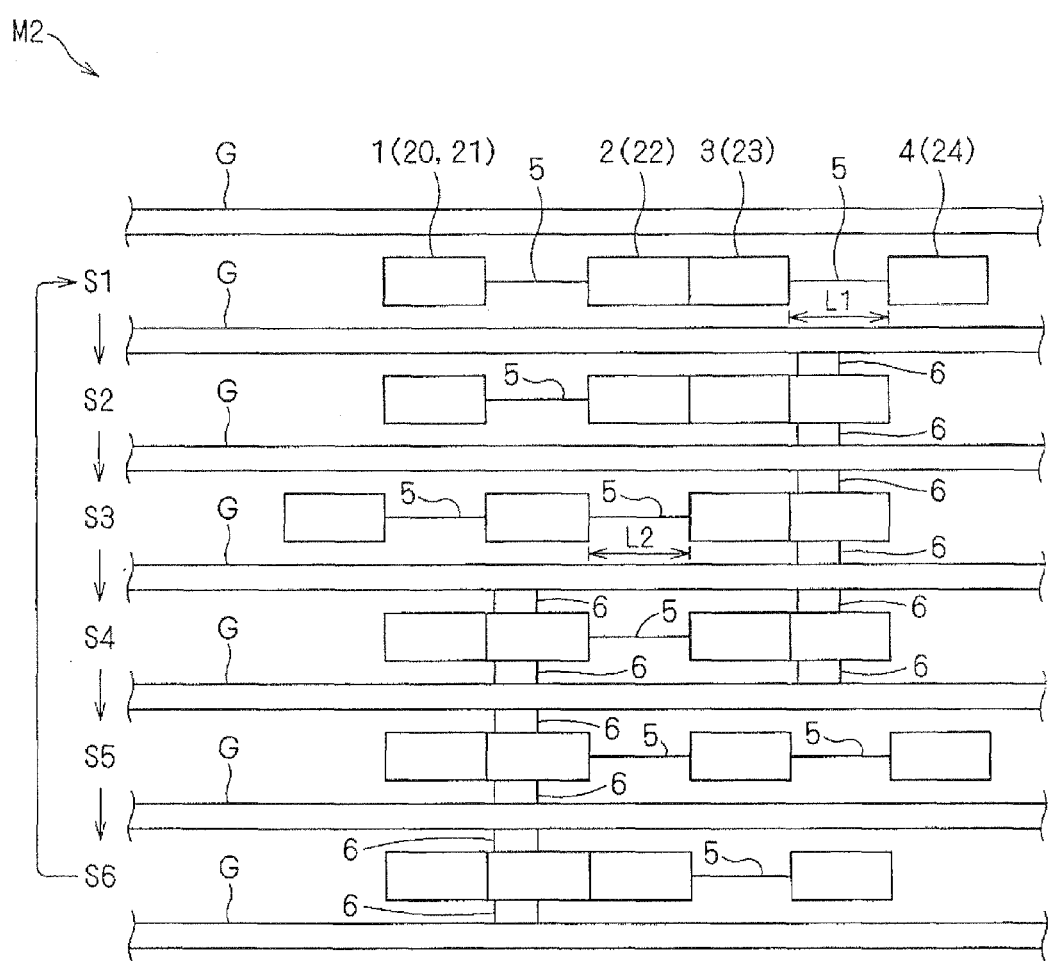
FIG. 6 is a pattern diagram showing the other moving method.

Next, using FIG. 6, the other moving method M2 is described. In the top and bottom of the moving device A in the figure, the wall G inside of a pipe line is expressed. And, the linear state of the engaging member 6 is not shown in the figure, and only the aspect of the engaged state with the inside of a pipe line by bending is shown by the belt shape portion. For example, the belt shape portion extending toward the inside of the pipe line from the top and bottom of the segment 4 in the state S2 of FIG. 6 expresses the state in which the engaging member 6 bends and engages with the inside of the pipe line. In the moving method M2, the extension/retraction motion of the extendable member 5, 5 is divided into the case for the bending of the engaging member 6 and for the moving motion (forward/backward movement) of the moving device. In other words, the extension/retraction motion for bending is a motion to obtain the engaging force with the inside of the pipe line by the bending of the engaging member 6, and that for the moving motion is a motion to make move the device toward the moving direction by using as a scaffold the portion where the engaging force with the inside of the pipe line by the engaging member 6 is working. For example, the extension/retraction between the second segment 2 and the third segment 3 where the engaging member 6 is not bridged does not contribute to the engaging in the pipe line. Hence, the extension/retraction motion of this portion can be specialized in the motion for moving the moving device. More specifically, by making large or making small the extension/retraction motion of this portion, the moving distance within one cycle of the device can be changed. Such making large or small of the extension/retraction as desired is difficult to be carried out by the extension/retraction motion for bending which is intended to obtain a predetermined engaging force with the pipe line. Additionally, when the inner diameter of a pipe line is large, a large stroke is required so as to make the engaging member protrude outward in the inside of the pipe line, in which case, the extension/retraction motion for bending to obtain the engaging force also contributes the movement of the moving device.

In the moving method M2 shown in FIG. 6, it begins from the state that the first the engaging member 6, 6 is extended, and the first segment 1 and the forth segment 4 are extended right and left (starting state S1). From the starting state S1, firstly, the forth segment 4 is pulled toward the third segment 3 (process S2). By the process S2, the engaging member 6 obtains the engaging force by bending to contact with the inside of the pipe line. Then, the third segment 3 make the first segment 1 and the second segment 2 move forward using as a scaffold the portion where the engaging force is working leaving the interval between those segment extended (process S3). The stroke of the third segment 3 in the process S3 can be lengthened or shortened than the extension/retraction interval L1 as in the moving method M1. In other words, when a large moving distance by one cycle is desired to obtain, the stroke may be lengthened, and when the forward movement is desired after the secure engagement of the engaging member 6, the stroke may be shortened. Thus, the stroke L1 required for the bending of the engaging member 6 and the stroke L2 related to forward/backward movement of the moving device can be set according to the used condition of the device.

After that, from the process 3, the first segment 1 is pulled toward the second segment 2 (process S4). In the process S4, the engaging force is obtained from the inside of the pipe line by the before-and-after two engaging member 6, 6. Then, the extendable member 5 between the third segment 3 and the forth segment 4 is extended, and the forth segment 4 is departed from the third segment 3 (process S5). And then, the extendable member 5 between the second segment and the third segment 3 is retracted, and both the third segment 3 and the forth segment 4 are pulled toward the second segment 2 (process S6). After this, the first segment 1 is departed from the second segment 2, returning to the initial state S1.

Figure 7:
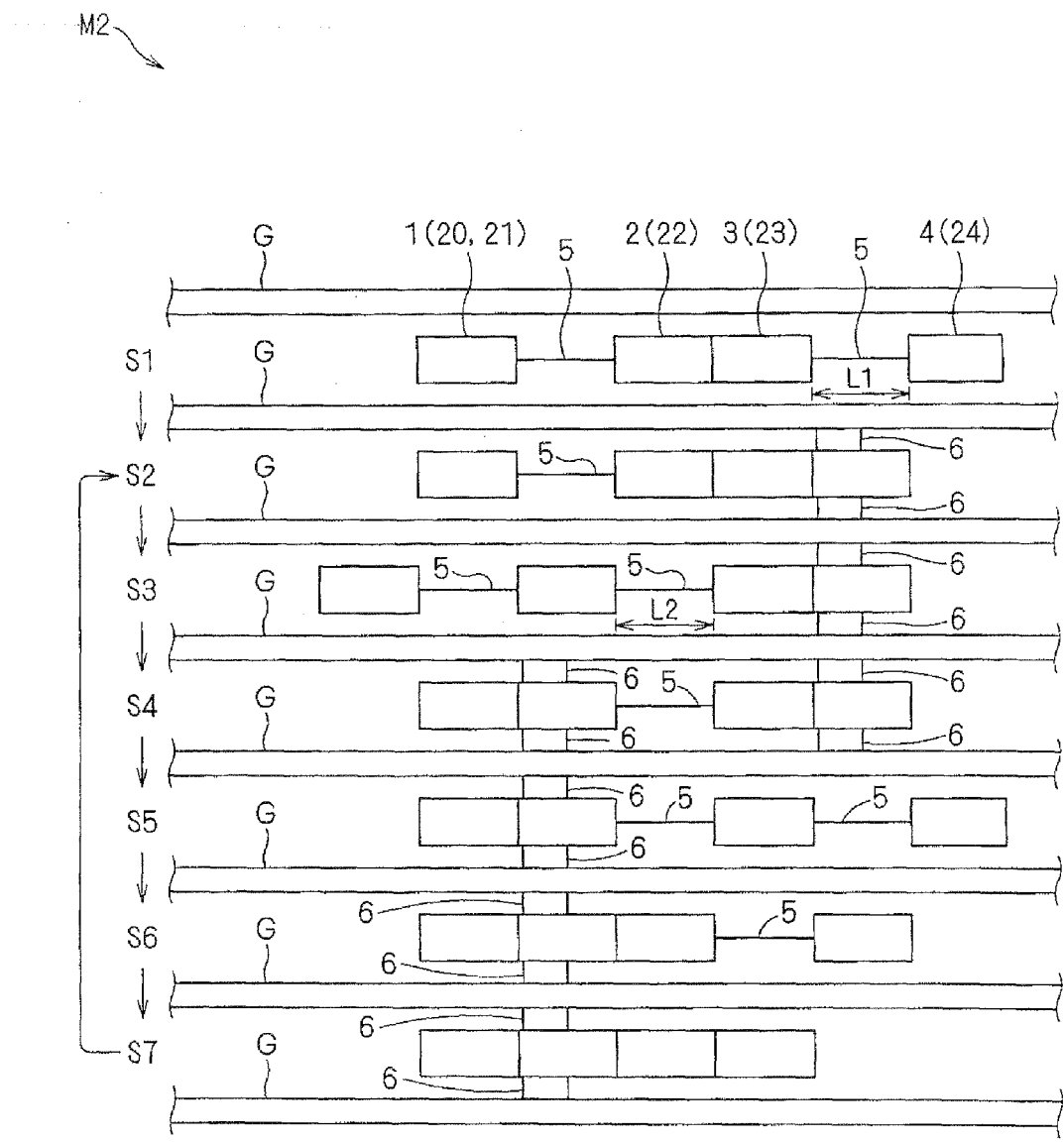
FIG. 7 is a pattern diagram showing further the other moving method.

In FIG. 7, another moving method M3 of the moving device A is shown. The moving method M3 is the same motion until the state S6 of the moving method M2. After the state S6, the forth segment 4 is pulled toward the third segment 3 (state S7). Then, the motions in the sequence of the state S2-S7 are repeated. Thus, the cycle of the state S2-S7 is repeated to move. Both the moving method M2, M3 make six motions be as one cycle to move.

According to the moving method M1, since one cycle is completed by four motions from the state S1 to S5, the motion is quick. However, since the strokes of all the extendable members 5, 5, 5 are same, the largeness of the engaging force with the inside of a pipe line, or a moving distance per one cycle etc. must be determined at the same time. And, according to the moving method M2, in the state S1, S6, there is a state in which the engaging member 6 does not engage with the inside of the pipe line. Therefore, it cannot ascend a vertical wall surface. Further, according to the moving method M3, in the state S7, there is a state in which all of the extendable means 5, 5, 5 retracts and four segments congregate in one. Depending on the pipe line, there may be a case that such congregation into one can not be done. Thus, since they have good and bad points, it is preferable to choose the most suitable moving method corresponding to the condition to be used.

The above described forward movement/backward movement is same with the case that it moves in a pipe line which is narrow and elastic as in the intestine. In the intestine, the moving device is enclosed so as to be compressed by the wall surface of the intestine. In such compressed condition also, by providing the portions for cramping up and supporting locally in the intestine to the moving device, a portion of high engaging force is yielded, and the portion where the engaging force is relatively weak compared with the supporting portion can move.

In this embodiment, it consists of four segments, but the number of the segment may be, for example, 5 or 10 being connected in series to carry out the above described moving motion. Since, in this case, by changing the number of the segment to be moved in every process, the engaging force with the inside of the pipe line can be changed, it can respond to the change of the engaging force with the inside of the pipe line. Moreover, in the one moving device, a plurality of the segments can be moved in one process at the same time, and further, a plurality of moving portions can be provided in one process. And, in the each segment, the engaging members 6 to increase the engaging force with the inside of the pipe line can be also attached, in which case, the engaging force is increased, and the number of the segments and the weight can be reduced, thereby it becomes a smaller and easy-to-use device.

Further, when the motion of the segments become complicated, if a controller is equipped, which can execute the above described pattern responding to the needs such as the condition of the inside of pipe lines and the moving speed by memorizing the motion pattern of several segments in a memory medium, it can addresses various insides of pipe lines. When it is constituted as this, if the engaging forces of the each segment with the inside of pipe lines are not about equal, by memorizing the engaging force in the above memory medium etc. It is possible to control the moving device in order to operate securely. In this memory device, it is also possible to memorize the previous movement data etc. and to reproduce it.

Figure 8:
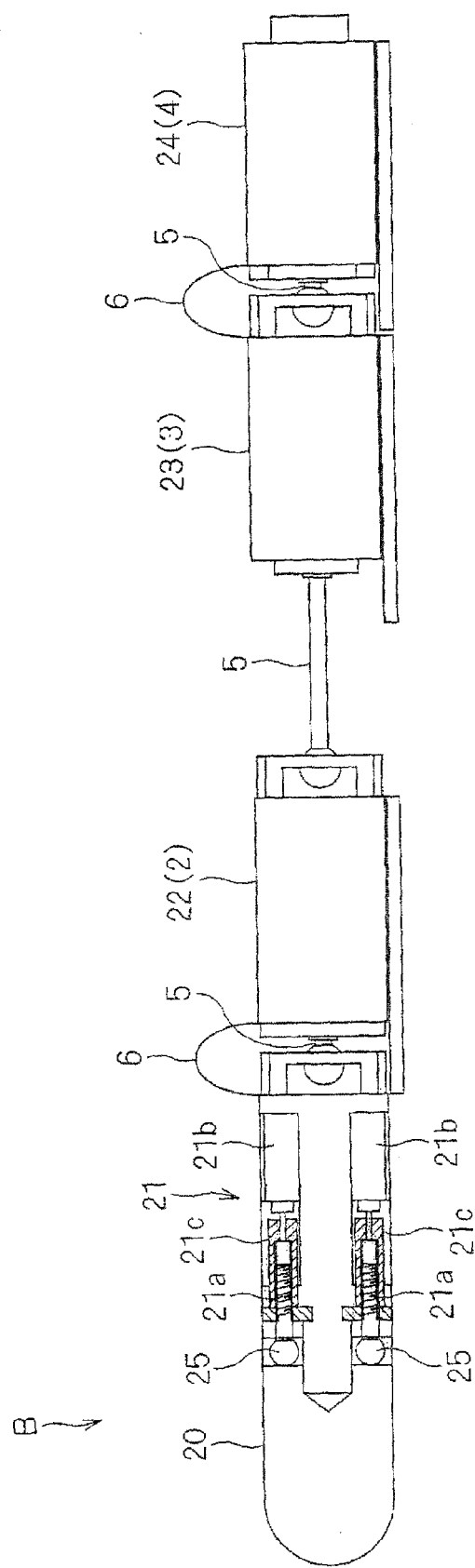
FIG. 8 is a rough drawing showing an embodiment of the moving device.

Next, the moving device B shown in FIG. 8 is described. Since in the moving device B, there are many common portions with the above described moving device A, the description about the common portions are omitted giving the same reference numerals. The moving device B comprises, from the front end, a head (camera portion) 20, a first segment 1 having a body (swivel portion) 21, a second segment 22 following the first segment 1, a third segment 23 following the second segment 22, and the forth segment 24 of the rear end. Between the head 20 and the body 21, a joint portion 25 is arranged. Thereby the camera mounted in the head 20 or head itself inclines in order to be capable of changing the visual field.

In the camera portion 20, a camera is housed in its front end portion. Same as the moving device A, other than the camera, a touch switch, a cleaning nozzle or an air nozzle can be housed also. The camera portion 20 is arranged at the front of the body 21. The body 21 is interconnected to the head 20 by three extendable screw axes 21a. Those screw axes are arranged at equal intervals around the center axis of the rough cylindrical body 21. Those screw axes 21a are movable toward the axis direction by the rotation of the screw. And, the front end of the screw axes 21a, 21a, 21a are interconnected to the rear end of the camera portion 20 through ball joints 25, 25, 25 (joint portion) (only two of them shown in the figure). On the other hand, the rear ends of the three screw axes 21a are interconnected to the three motors 21b respectively. The motor 21b rotates a nut member 21c (female screw) screwing together with the screw axis 21a, making the screw axis 21a protrude from the body 21 and housed alternately. By changing the length of the protrusion of the three screw axes 21a by the three motors 21b, the head 20 can be inclined and the like to a desired direction in the pipe line. Additionally, the screw axis 21a, the female screw 21c and the motor 21b of this moving device B are a drive portion 26 (drive unit).

Figure 9:
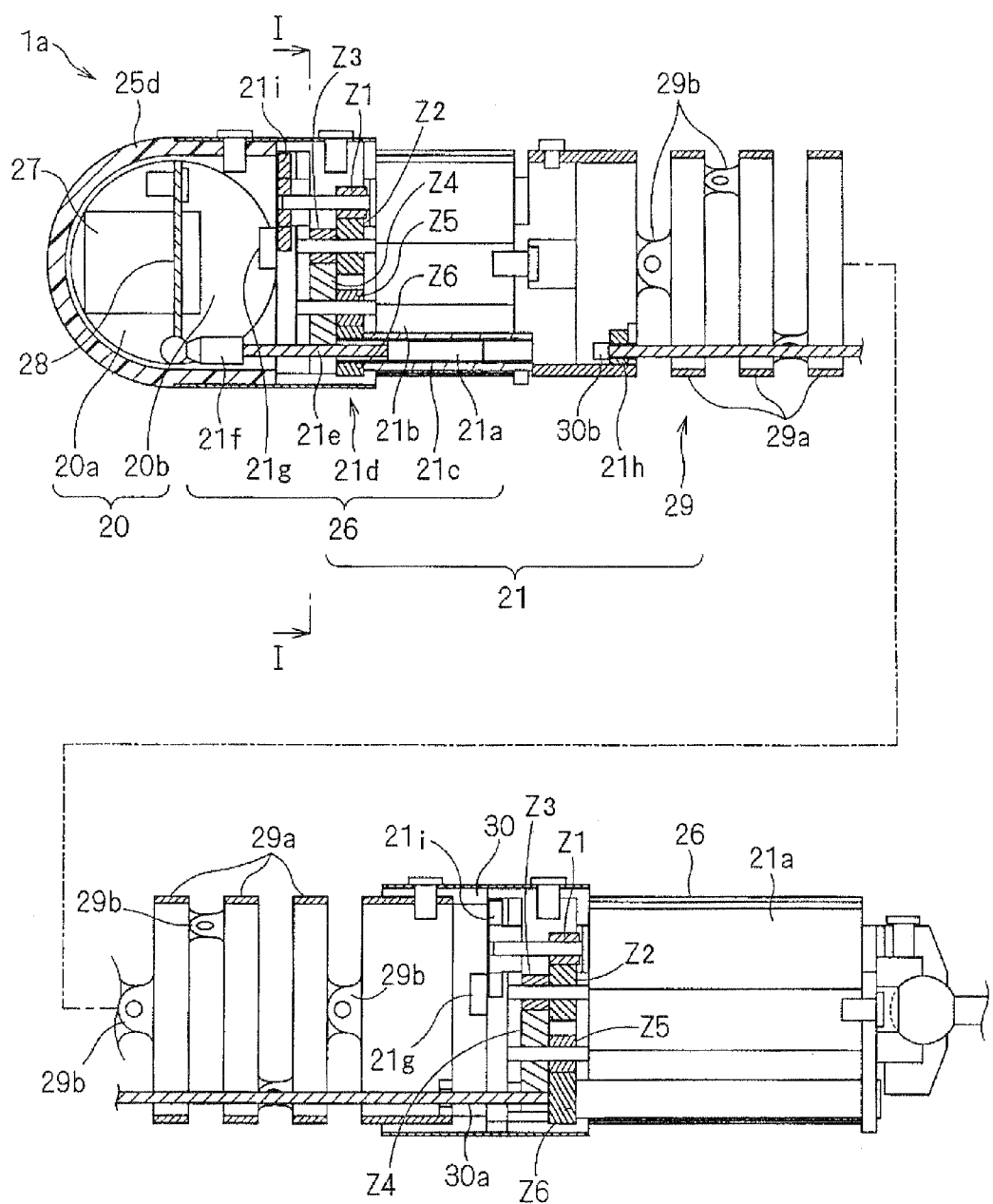
FIG. 9 is a partial cross sectional side view showing the other embodiment of the first segment.

In FIG. 9, the other embodiment of the first segment 1 is shown. Since the first segment 1a shown in FIG. 9 has many common portion with the above described first segment 1, the description is omitted giving the same reference numeral to the common portions. In the front end of the first segment 1, a dome portion 25d (joint portion) of semispherical shape formed by transparent synthetic resin etc. is provided. In the inner perimeter of the dome portion 25d, a spherical camera support portion 20 is housed slidably.

The camera support portion 20 is formed by, for example, stainless, titanium, or biocompatible metal. In this embodiment, the spherical camera support portion 20 is divided at the vicinity of the center into two semispherical portion 20a (front side), 20b (rear side). The front side spherical portion 20a is arranged so as to slidably contact with the inner surface of the dome 25d at the front side spherical surface. In the vertical surface side of the rear side, there is a portion recessed toward inside, and in the recessed portion, the camera body 27 is housed. And, from the back side of the camera body 27, a circular disk 28 is mounted to plug the recessed portion. In the circular disc 28, three holes 28a, 28a, 28a are formed at equal intervals in the vicinity of the periphery, and from these three holes 28a, slits 28b, 28b, 28b are formed to communicate the inside and outside of the holes 28a. The circular disc 28 is arranged so as to be sandwiched by the each vertical plane of the front side semispherical member 20a and the rear side semispherical member 20b.

The spherical surface of the semispherical portion 20b of the rear side contacts with the later described body 21. Hence the spherical camera portion 20 is arranged so as to be sandwiched slidably by the inside of the dome portion 25a and the body 21 side.

Figure 12:
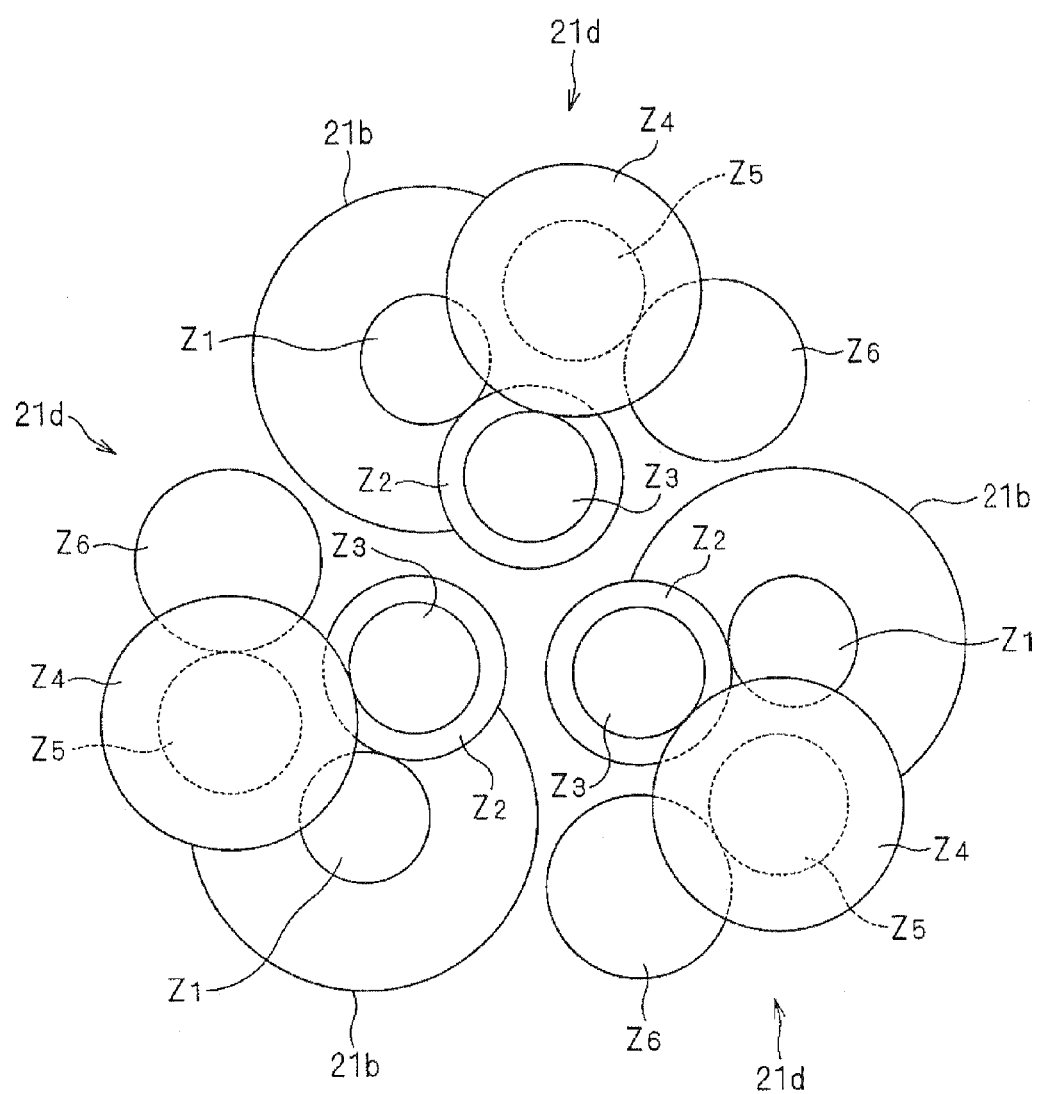
FIG. 12 is a rough I-I line cross sectional view of FIG. 9 showing the arrangement of the gear of the speed reducer.

The rotational movement from the motor 21b provided in the drive portion 26 is transmitted to the female screw 21c through a speed reducer 21d (see FIG. 12). And, by the rotation of the female screw 21c, the screw axis 21a moves back and forth. In the front end of the screw axis 21a, an inner cable 21e is locked, and when one or two inner cables 21e are pushed out, the remaining inner cables 21e are pulled in. As the inner cable 21e, a pull-cable may be used or a push-cable may be used.

As shown in FIG. 12, the shafts of the three motors 21b of the body 21 are arranged so as to be capable of obtaining a predetermined number of rotation by the speed reducer 21d, 21d, 21d. The speed reducer 21d is transmitted from a gear Z1 directly coupled to the motor shaft 21, to a gear Z2 whose diameter is a little larger than that of Z1, to a gear Z3 whose diameter is smaller than that of Z2, to a gear Z4 whose diameter is larger than that of Z3, to a gear Z5 whose diameter is smaller than that of Z4, to a gear Z6 (female screw 21c) whose diameter is larger than that of Z5, and is reduced its speed sequentially. Further, in the same axis with the gear Z1 of the speed reducer 21d and in the opposite end, a circular disc shape magnet 21i is mounted. The magnet 21i has a circular disc shape with its one side divided by the diameter being made to be N pole and another side to be S pole. A hall IC 21g is arranged so as to face the position slanted to either of the N pole or S pole of the magnet 21i. The S pole and the N pole of the magnet 21i pass through the hall IC 21g alternatively by every rotation of the magnet 21i. The hall IC 21g detects the change of magnetism and measures the amount of the rotation of the gear Z1. Thereby, the amount of pulling-pushing of the inner cable 21e later described is found.

Figure 11:
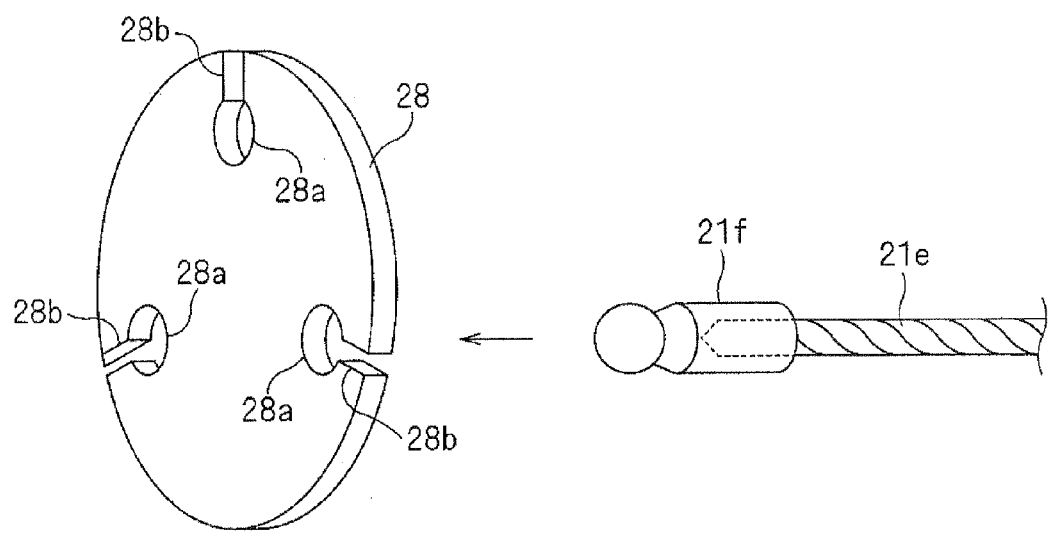
FIG. 11 is a rough side view showing the disc portion and end portion of FIG. 9.

In the front end of the inner cable 21e extending from the screw axis 21a of the body 21, an end portion 21f (see FIG. 11) having a spherical portion in its front end is fixed. The end portion 21f have the spherical portion of the front end and a portion extending backward a little constricted from the spherical portion, and at its rear end, the end of the inner cable 21e is cramped to fix. The inner cable 21e is let through from the slit 28b of the circular disc 28, and fixed by being hooked on the hole 28a of the circular disc 28 at the spherical portion of the end portion 21f. Returning to FIG. 9, the head 20 slides and turns in the dome portion 25d by the inner cable 21e being pushed and pulled.

Returning to FIG. 9, in the rear of the body 21, a flexible joint 29 is interconnected. In the rear of the flexible joint 29, a tail section 30 is interconnected. The flexible joint 29 consists of a plurality of annular members 29a, 29a-(see FIG. 10a). Those annular members 29a are interconnected mutually by one pair of supporting point 29b rotatably. Those annular members 29a are interconnected in series with the one pair of supporting point being staggered at about every 60 degrees (see FIG. 10b). Hence, whole of the flexible joints 29 can be smoothly curved to a desired direction. The plurality of the annular members 29a may be polygon such as hexagon in their cross section.

In the tail section 30 shown in FIG. 9, a drive portion 26 about similar to what is provided in the body 21 is provided. Hence, the same reference numeral is given to the same portion and the description is omitted. Three inner cables 30a, 30a, 30a are arranged at equal intervals around the axis headed toward the front from the tail section 30. The inner cables 30a pass through the inside of the flexible joint 29 and locked to the rear of the body 21. In the front end of the inner cable 30a of the tail section 30, a nipple end 30b is formed and locked to the cable lock portion 21h formed in the rear of the body 21. Moreover, in the tubular member 29a of the flexible joint 29, a cable guide 29c to pass through the inner cable 30a is provided (see FIG. 10b). Hence it is configured as thus, when the inner cable 30a is pushed or pulled, the flexible joint 29 can be curved to a desired direction.

The flexible joint 29 can change its length by changing the number of the annular member 29a. Moreover, since it uses the inner cable 30a, the force can be transmitted even in a curved shape.

Figure 13:
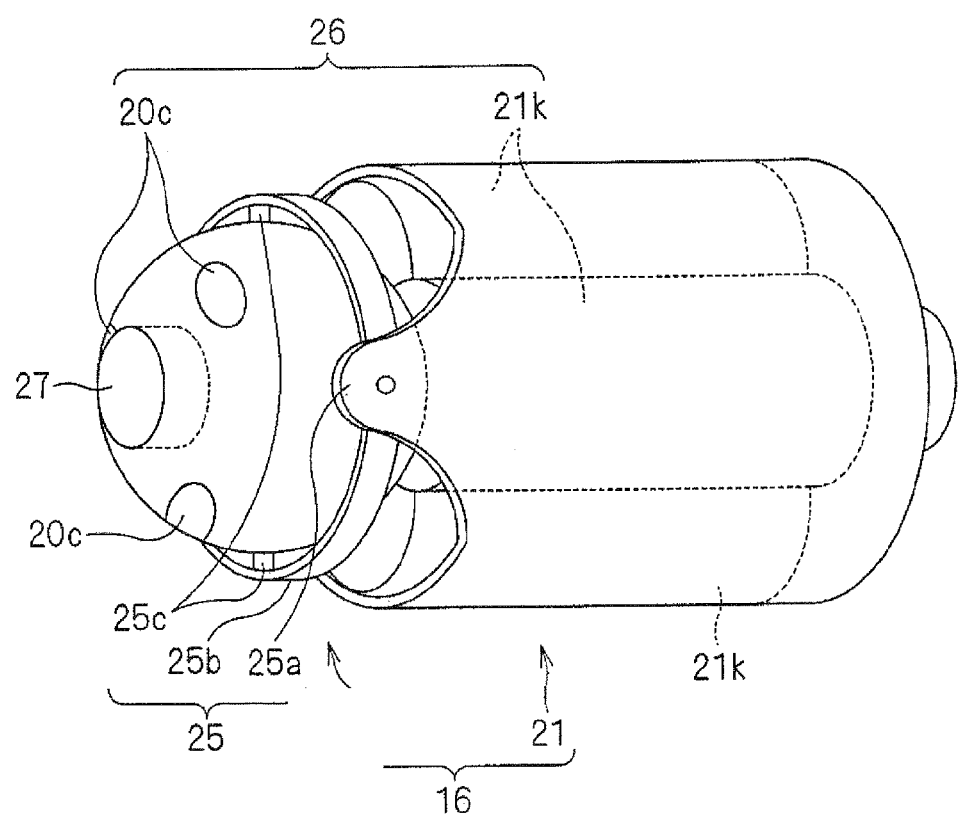
FIG. 13 is a perspective view showing further the other first segment.

In FIG. 13, the other embodiment of the first segment 1 is shown further. Since the first segment 1b shown in FIG. 13 is about similar to the first segment 1, 1a, the description is omitted giving the same reference numeral to the same portion. In the first segment 1b, the spherical head 20 is interconnected turnably to the body 21 by an universal joint 25 (joint portion). Moreover, as described later, three magnets 20c, 20c, 20c are provided in the head 20, and in the body 21, three electromagnets 21k, 21k, 21k are equipped so as to correspond to the magnets 20c of the head 20. Those magnets 20c and the electromagnets 21k constitute the drive portion 26, and by the drive portion 26, the head 20 turns against the body 21. In addition, the number of the magnets 20c is preferable to be more than three, and being large in the number makes it possible to perform the fine adjustment of the head 20. And, the number of the electromagnets 21k is also preferable to be more than three. The number of the magnets 21k and the number of the electromagnets 21k are preferable to be the same number.

The universal joint 25 consists of one pair of bosses 25a, 25a protruding from the front of the body 21, and a ring-shaped member 25b pivoted by the bosses 25a, 25a. The center of ring-shaped member 25b is arranged on the axis line connecting the one pair of bosses 25a, 25a. In the ring-shaped member 25b, one pair of pivot supporting members 25c is formed, and the axis line connecting the pivot supporting members 25c, 25c passes through the center of the head 20, and pivoting the head 20 turnably by crossing orthogonally the axis line connecting the bosses 25a, 25a.

As shown in FIG. 14, the magnet 20c of the head 20 is arranged at equal intervals (see FIG. 14b) radially around the axis of the head 20 so as to surround the camera body 27. In this embodiment, since the number of the magnets 20c is three, they are arranged at 120 degrees interval viewed from the front side (FIG. 14b). The camera body 27 is inserted into the front end of the head 20, and fixed as it is. Moreover, in the opposite side of the magnets 20c of the head 20 and the camera body 27, a weight 20d is arranged to balance the back and forth of the spherical head 20. Further, in the rear spherical surface of the head 20, a plurality of recessed portions 20e, 20e, 20e (in the figure, three) is formed.

In addition, in the electromagnet 21k provided in the head 21, same as the above described motor 21b, three electromagnets 21k, 21k, 21k are arranged at equal intervals around the axis in the moving direction. Moreover, in the front of the body 21, a detent ball 31 energized toward the head 20 is provided and engages with the recessed portion 20e of the head 20. Thereby, the positioning of the head 20 becomes easy. The detent ball 31 comprises a detent axis 31a inserted into the axial direction of the body 21 and a coil spring 31b arranged around the detent axis 31a. The front end of the coil spring 31b is locked to the step in front of the detent axis 31a. On the other hand, the rear end is locked to the body 21 and energizes the detent 31a forward.

The head 20 can incline the camera body 27 toward the direction of the attracting electromagnet 21k by the magnetic force of the electromagnet 21k of the body 21 which attracts or repels the electromagnet 20c of the head 20. In this occasion, by exciting the two electromagnets at the same time, it can be inclined also in the direction between these electromagnets 21k.

Next, using FIG. 15a, the second segment 22 is described. As for the forth segment 24, since it is similar with the second segment 22, the description is omitted. Additionally, as for the structure of the extendable member 5 of the second segment 22, it is same as that described by FIG. 2, and the aspect of the motion of the engaging member 6 responding to the extension/retraction of the extendable member 5 is same as that described by FIG. 3. And, the magnet 18 arranged in the extendable member 5 of the second segment 22 is not formed to be cylindrical as that of the moving device A (see FIG. 2), and a platy magnet member is interconnected to the ball 19, and is arranged so that it slides between the driver 10 and the casing 11 by the movement of the male screw 14. In FIG. 2, the male screw 14 is rotated by the one motor 13, but in the embodiment of FIG. 15, three motors 13, 13, 13 are arranged around the male screw 14, and the center gear 14a is rotated by the gear 13a provided respectively in the motor axis of the three motors 13. In the central opening of the center gear 14a, a nut portion screwing together with the male screw 14 is formed, and the male screw 14 is pushed out from or pulled in to the casing 11 by the rotation of the center gear 14a. Thus, since the male screw 14 is made to be movable in the axis direction by the three gears 13a, the rotation of the male screw becomes stable.

In the moving device B of FIG. 8, the second segment 22 and the forth segment 24 is a portion used for obtaining the engaging force in pipe lines. Hence, if an enough engaging force is obtained, an excess stroke is not necessary for the forward movement and the backward movement. In other words, since the moving device moves by the moving method M2 (see FIG. 6), M3 (see FIG. 7), it is enough to be possible to obtain the inner diameter of the pipe line in which it is moving or a sufficient bend of the engaging member 6 to obtain the frictional force necessary for moving, the extending/retracting interval of the extendable member 5 in between the front first segment 1 may be small when the inner diameter of the pipe line is small.

Next, using FIG. 15b, the third segment 23 is described. Since the third segment 23 is almost same as the third segment 3 of FIG. 2, the description about the same portion is omitted. The third segment 23 of FIG. 15b is a portion for moving the moving device B forward. Hence, it is possible to construct so that a stroke larger than the distance with which the extendable member 5 of the above described third segment 3 extends/retracts at a time can be obtained. Additionally, the portion of the magnet 18 is same as the above described second segment 22.

Next, using FIG. 16, the detection of magnetism of the position sensor 12 of the second segment 22 and the third segment 23 is described. As described above, in the two second segments 22, 23, the stroke of the each extendable member 5 is different. Hence, when the stroke is small, the position sensor 12 must be made to be capable of detecting surely the magnetism of the magnet 18. On the other hand, when the stroke is long, since there is a case that the interval of the stroke is longer than the interval at which the hall element of the position sensors 12 are arranged, an artifice in the arrangement of the magnetism on the magnet 18 so as to facilitate the detection of the end of stroke is necessary. As shown in FIG. 15, the position sensor 12 is composed of two elements 12a and 12b. These two elements 12a, 12b carry out ON-OFF when detecting the magnetism, and the operating status of the extendable member 5 is checked by the detected pattern. When those elements 12a, 12b detects, for example, the magnetic change from S to N or from N to S, at every change, it switches transmitting signals to the driver 10 from ON to OFF or from OFF to ON. Additionally, the element 12*a* is arranged in the front of the forward direction of the movement and the element 12*b* is arranged in the rear. The left figures of FIG. 16 show the aspect of the operation of the position sensor 12 and the magnet 18, and the right figures which the arrows indicate are respectively the summary of the detected results of ON/OFF of the elements 12*a*, 12*b* in the operating status.

FIG. 16*a* shows the magnet 18 and the position sensor 12 of the third segment 23. The magnet 18 of the third segment 23 is magnetized to be magnetism N broadly in the central portion, and the both end portions of the magnetism N are magnetized to be S. The portion magnetized to be magnetism N is magnetized so as to be larger than the interval at which the element 12*a* and the element 12*b* are arranged. First, in the state (P1 of FIG. 16*a*) that extendable member 5 of the third segment 23 is retracted, the element 12*a* is OFF and the element 12*b* detects ON. When the extendable member 5 extends, since the element 12*a* is positioned in the portion whose magnetism is magnetized to be from magnetism S to N, the element 12*a* becomes ON (P2 of FIG. 16*a*) by the magnetism change. Then, when the extendable member 5 further extends, the rear element 12*b* is switched to be OFF by detecting the magnetism change from magnetism S to N (P3 of FIG. 16*a*). When the extendable member 5 retracts, the element 12*a* becomes OFF and the element 12*b* becomes ON by the inverse sequence to that described above.

FIG. 16*b* shows the magnet 18 and the position sensor 12 of the second segment 22 and the forth segment 24. Since the strokes of the second segment 22 and the forth segment 24 are narrow, the magnetized magnetism in the magnet is separated to be S and N right and left. First, when the extendable member 5 is retracted, the both elements 12*a*, 12 *b* are in the state of OFF (P1 of FIG. 16*b*). When the extendable member 5 extends from there, initially, the rear element 12*b* is switched from OFF to ON by detecting the magnetism change (P2 of FIG. 16*b*). Then, when the extendable member 5 further extends to reach the tail end, the magnetism of the front element 12*a* changes and the signal becomes ON (P3 of FIG. 16*b*). Thus, since the distance of the stroke is short, the tail end of the stroke is detected by the magnetism change of the two elements 12*a*, 12*b*.

The invention claimed is:

1. A moving device in a pipe line, comprising;
more than three segments including a front segment arranged in serial;
an extendable interconnecting means to connect adjacent segments; and
an engaging force changing means to change an engaging force of the segment which is to be moved with an inside of the pipe line to a smaller force, smaller than the engaging force of the remaining segment with the inside of the pipe line;
wherein the moving device moves back and forth by extending or retracting the extendable interconnecting means,
wherein the front segment has a head part, a body part, a joint part to turn the head part centering around the body part, and a drive unit to move the head part around the body part,
wherein the drive unit has a magnet provided in the head part and an electromagnet provided in the body part, and
wherein the head part moves around the body part by attracting or repelling the magnet of the head part by the magnetic force of the electromagnet.

2. A moving device in a pipe line according to claim 1,
wherein the joint part is a universal joint,
wherein at least three magnets are provided around an axis of a moving direction of the head part at equal intervals, and plural of the electromagnet is provided around the axis of the moving direction of the body part at equal intervals,
wherein numbers of the magnet and the electromagnet are same.

3. A moving device in a pipe line according to claim 2,
wherein the head part is formed spherically, and a plurality of recessed portions are formed on the rear spherical surface of the head part, and
wherein a detent ball, which is energized toward the head part and which is engaged with the recessed part, is provided in a front of the body part.

4. A moving device in a pipe line according to claim 1,
wherein more than four segments are arranged in serial,
wherein an engagement member bridging adjacent segments is provided between at least more than two adjacent segments, and when the extendable interconnecting means interconnecting the adjacent segments bridged by the engagement member retracts, the engagement member bends and a bended part of the engagement member protrude outwardly engaging with the inside of the pipe line.

5. A moving device in a pipe line according to claim 4,
wherein the front segment, a second segment a third segment, and a fourth segment are arranged in serial,
wherein the engagement member bridging the adjacent segments is provided between the front segment and the second segment, and the third segment and the fourth segment.

6. A moving device in a pipe line according to claim 1,
wherein the head part of the front segment is mounted with a camera, a cleaning nozzle, or a touch switch.

7. A moving device in a pipe line comprising;
more than three segments including a front segment arranged in serial;
an extendable interconnecting means to connect adjacent segments; and
an engaging force changing means to change an engaging force of the segment which is to be moved with an inside of the pipe line to smaller force, smaller than the engaging force of the remaining segment with the inside of the pipe line;
wherein the moving device moves back and forth by extending or retracting the extendable interconnecting means,
wherein the front segment has a head part, a body part, a joint part to turn the head part centering around the body part, and a drive unit to move the head part around the body part,
wherein the drive unit has an inner cable interconnecting the head part and the body part, an inner cable locking portion provided in the head part, a motor portion provided in the body part, and
wherein the head part is turned around the body part by pulling in or sending out the inner cable by the motor portion.

8. A moving device in a pipe line according to claim 7,
wherein the inner cable, the inner cable locking portion of the head part, and the motor portion of the body part as a set are arranged respectively around an axis of a moving direction and more than three sets are arranged respectively at equal intervals in the axis of the moving direction.

9. A moving device in a pipe line according to claim 8, wherein the front segment, a second segment a third segment, and a fourth segment are arranged in serial,
  wherein the engagement member bridging the adjacent segments is provided between the front segment and the second segment, and the third segment and the fourth segment.

10. A moving device in a pipe line according to claim 7 wherein more than four segments are arranged serially,
  wherein an engagement member bridging adjacent segments is provided between at least more than two adjacent segments, and when the extendable interconnecting means interconnecting the adjacent segments bridged by the engagement member retracts, the engagement member bends and a bended part of the engagement member protrude outwardly engaging with the inside of the pipe line.

11. A moving device in a pipe line according to claim 7, wherein the head pert of the front segment presents a rough spherical shape, and is mounted with a camera, a cleaning nozzle, or a touch switch,
  wherein the joint part is extended from the body part to hold the head part, the joint part is a sliding member which covers the periphery of the head part, the head part is arranged to slide an inside surface of the sliding member.

* * * * *